US012582360B2

(12) United States Patent
Rahamim

(10) Patent No.: US 12,582,360 B2
(45) Date of Patent: Mar. 24, 2026

(54) MEANS TO ACCURATELY PREDICT, ALARM AND HENCE AVOID SPORT INJURIES AND METHODS THEREOF

(71) Applicant: GAINGUARD LTD., Rehovot (IL)

(72) Inventor: Tamir Rahamim, Rehovot (IL)

(73) Assignee: GAINGUARD LTD., Rehovot (IL)

( * ) Notice: Subject to any disclaimer, the term of this patent is extended or adjusted under 35 U.S.C. 154(b) by 490 days.

(21) Appl. No.: 17/927,407

(22) PCT Filed: May 24, 2021

(86) PCT No.: PCT/IL2021/050606
§ 371 (c)(1),
(2) Date: Nov. 23, 2022

(87) PCT Pub. No.: WO2021/240511
PCT Pub. Date: Dec. 2, 2021

(65) Prior Publication Data
US 2023/0200749 A1     Jun. 29, 2023

Related U.S. Application Data

(60) Provisional application No. 63/029,576, filed on May 25, 2020.

(51) Int. Cl.
A61B 5/00          (2006.01)
A61B 5/0205          (2006.01)
(Continued)

(52) U.S. Cl.
CPC ............ A61B 5/746 (2013.01); A61B 5/0022 (2013.01); A61B 5/0205 (2013.01);
(Continued)

(58) Field of Classification Search
CPC ..... A61B 5/746; A61B 5/0022; A61B 5/0205; A61B 5/02416; A61B 5/7275;
(Continued)

(56) References Cited

U.S. PATENT DOCUMENTS 5,474,083 A     12/1995   Church et al.
10,610,146 B1    4/2020   Kahn et al.
(Continued)

FOREIGN PATENT DOCUMENTS

CN        206792389 U   * 12/2017
WO        2019026092 A1    2/2019

OTHER PUBLICATIONS

Maffulli et al. (2015). Muscle Injuries: A Brief Guide to Classification and Management. Transl Med UniSa. Sep. 1, 2014;12:14-8. PMID: 26535183; PMCID: PMC4592039.
(Continued)

*Primary Examiner* — Brian A Zimmerman
*Assistant Examiner* — Anthony D Afrifa-Kyei
(74) *Attorney, Agent, or Firm* — The Roy Gross Law Firm, LLC; Roy D. Gross

(57)          ABSTRACT

Multiple-sensor IoT devices are worn by users, each device containing one or more physiological and/or environmental sensors. The devices communicate with an external smart device that collects readings from the sensors. An algorithm module analyzes the readings and generates alerts to notify users if indices of the readings, and/or of parameters computed therefrom, are in potentially dangerous ranges.

20 Claims, 5 Drawing Sheets

(51) Int. Cl.
A61B 5/024 (2006.01)
G16Y 40/10 (2020.01)

(52) U.S. Cl.
CPC ......... *A61B 5/02416* (2013.01); *A61B 5/7275* (2013.01); *A61B 2503/10* (2013.01); *G16Y 40/10* (2020.01)

(58) Field of Classification Search
CPC ......... A61B 2503/10; A61B 5/00; A61B 5/72; A61B 5/7271; A61B 5/02055; A61B 5/14551; A61B 5/14552; A61B 5/4845; A61B 5/4848; A61B 5/7282; A61B 5/7425; A61B 5/747; A61B 2562/0238; A61B 5/0261; A61B 5/0816; A61B 5/01; A61B 5/1112; A61B 5/1118; A61B 5/14532; A61B 5/165; A61B 5/168; A61B 5/4306; A61B 5/4839; A61B 5/4866; A61B 5/6898; A61B 5/7239; A61B 5/7405; A61B 5/742; A61B 5/743; A61B 5/7435; A61B 5/7475; A61B 2505/07; A61B 2560/0295; A61B 2560/0475; G16Y 40/10; G16H 20/17; G16H 40/63; G16H 40/67; G16H 50/30; G16H 20/30; G16H 20/00; G16H 20/60; G08B 21/043; G08B 21/00; G08B 21/02; G08B 21/04; G08B 21/0407; G08B 5/225; G08B 21/0446; G08B 21/0453; G08B 27/005; G08B 5/002; G08B 21/0438; G08B 21/182; H04W 4/02; H04W 4/90; A61M 5/1723; A61M 5/5086; A61M 2005/1726; G06F 3/04817; G06F 3/04847

See application file for complete search history.

(56) References Cited

U.S. PATENT DOCUMENTS

| 2015/0289823 | A1* | 10/2015 | Rack-Gomer | ....... A61B 5/6898 600/365 |
|---|---|---|---|---|
| 2016/0335871 | A1 | 11/2016 | Kim et al. | |
| 2019/0362612 | A1 | 11/2019 | Myers et al. | |
| 2021/0321953 | A1* | 10/2021 | Panneer Selvam | .... A61B 5/681 |

OTHER PUBLICATIONS

PCT International Search Report for International Application No. PCT/IL2021/050606, mailed Nov. 1, 2021, 6pp.
PCT Written Opinion for International Application No. PCT/IL2021/050606, mailed Nov. 1, 2021, 5pp.
PCT International Preliminary Report on Patentability for International Application No. PCT/IL2021/050606, completed Nov. 15, 2022, 8pp.

* cited by examiner

115

200

| | |
|---|---|
| PROVIDING A NETWORK FOR ALERTING USERS OF DANGEROUS PHYSIOLOGICAL ACTIVITY | ~ 205 |

| | |
|---|---|
| ARRANGING A SENSOR HIVE WITH A SLAVE AND CHILD DEVICES | ~ 210 |

| | |
|---|---|
| THE SLAVE DEVICE RECEIVING LIVE READINGS FROM PHYSICAL SENSORS OF THE CHILD DEVICES | ~ 215 |

| | |
|---|---|
| A SMART DEVICE RECEIVING THE LIVE SENSOR DATA OF THE WEARABLE MULTI-SENSORS IOT DEVICES FROM THE SLAVE DEVICE | ~ 220 |

| | |
|---|---|
| THE SMART DEVICE MANAGING A POWER-SAVING PROTOCOL OF THE SENSOR HIVE | ~ 225 |

| | |
|---|---|
| VIRTUAL SENSORS OF AN ALGORITHM MODULE EACH COMPUTING A PARAMETER AS A FUNCTION OF PHYSICAL SENSOR READINGS AND/OR OTHER VIRTUAL SENSOR READINGS | ~ 230 |

| | |
|---|---|
| THE ALGORITHM MODULE, IN COMMUNICATION WITH A CLOUD SERVER, GENERATING WARNINGS AS A FUNCTION OF THE PARAMETERS AND PAST/GLOBAL DATA FROM THE CLOUD SERVER | ~ 235 |

| | |
|---|---|
| THE ALGORITHM MODULE SENDING THE WARNINGS TO THE SMART DEVICE | ~ 240 |

| | |
|---|---|
| THE SMART DEVICE PACKAGING THE WARNINGS AND SENDING THE PACKAGE TO THE SLAVE DEVICE | ~ 245 |

Fig. 4

MEANS TO ACCURATELY PREDICT, ALARM AND HENCE AVOID SPORT INJURIES AND METHODS THEREOF

CROSS REFERENCE TO RELATED APPLICATIONS

This application is a National Phase of PCT Patent Application No. PCT/IL2021/050606 having International filing date of May 24, 2021, which claims the benefit of priority of U.S. Provisional Patent Application No. 63/029,576, filed May 25, 2020, the contents of which are all incorporated herein by reference in their entirety.

FIELD OF THE INVENTION

The present invention generally pertains to real-time, on-line wireless, small, light and portable, affordable and safe means and methods configured to accurately predict, alarm and hence avoid future injuries before actual damage occurs, e.g., in the fields of sports, rehabilitation, employment etc.

BACKGROUND OF THE INVENTION

Skeletal muscle injuries represent a great part of all traumas in sports medicine, with an incidence from 10% to 55% of all sustained injuries. They should be treated with the necessary precaution since a failed treatment can postpone an athlete's return to the field with weeks or even months and increase the risk of re-injury. A number of factors predispose an athlete to muscle strains: inadequate warm-up; insufficient joint range of motion; excessive muscle tightness; fatigue/overuse/inadequate recovery; muscle imbalance; previous injury; faulty technique/biomechanics; and spinal dysfunction. Both for acute and chronic injuries, thorough subjective examination is primary in identifying muscle injuries. Particular attention to the history of occurrence of the trauma is needed. A clinical examination and testing of the muscle function together with the patient's recollection of what happened, are mostly sufficient for making the right diagnosis. In some cases, additional tests (MM, x-ray, ultrasound, CT scan) may be required to determine the extent of the injury or to identify possible additional injuries; see Maffulli, Nicola, et al. "Muscle injuries: a brief guide to classification and management." *Translational Medicine@ UniSa* 12 (2015): 14. Those diagnostic means are provided useful for off-line muscle analysis.

U.S. Pat. No. 5,474,083 discloses on-line cordial diagnostic means provided as a microprocessor-based belt-like system. This system utilizes an electromyographic sensor to monitor muscle force for lift training and exercise training. The exercise training embodiment has a bar graph display displaying muscle intensity and two light emitting diodes alerting a user when to contract or relax a monitored muscle group. To ensure actual usage the belt is also provided with temperature and/or motion sensors.

It is hence a long felt need to provide an on-line wireless portable, affordable, safe and accurate means configured to predict future injuries before actual damage occurs, e.g., in the fields of sports, rehabilitation, employment etc.

SUMMARY OF THE INVENTION

In some embodiments, the invention provides a system for detecting physiological indices in a user (1), alarming and thereby preventing injuries, characterized by a. a wearable multiple-sensors IoT device comprising one or more sensors selected from either Group A or [Group A and Group B]; the sensors of Group A are all the three (i) muscle intensity sensor, (ii) blood pulse sensor, and (iii) skin thermometer; the one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof;

b. a communicator in a continuous or a semi- (interval) continuous connection with the multiple-sensors; the communication is provided in direct or mediated protocols and means thereof;

c. a computer readable database for storing the hereto diagnosed data; and d. a processor configured for
   i. computing one or more indices from parameters measured by or computed from the sensors;
   ii. comparing each of the indices with one or more retrievable limits of the index, the limits defining at least one allowable range and at least one potentially dangerous range of the index;
   iii. if the hereto measured index is within the at least one allowable range, storing the index in the database; and
   iv. if the hereto measured index is within the at least one potentially dangerous range, both storing the index in the database and alerting the user; and e. one or more alarms for the alerting of the user, including light and noise emitters, vibrators or actuators, and any combination thereof optionally, one or more alarms is configured to alert the user thereby stopping one or many potentially dangerous activities; optionally, additionally or alternatively, one or more alarms is configured to alert user's immediate surroundings, including user's interfaces, user's guides and a combination of the two; optionally, additionally or alternatively, one or more alarms is configured to alert in one or more remote locations, including a remote instructor, ambulance team, physician, friends, family and any combination thereof.

In some embodiments of the system, the blood pulse sensor comprises a PPG, a pulse oximeter, or any combination thereof.

In some embodiments of the system, the indices and limits are selected from a group consisting of an intensity index and limit, a preparation index and limit, and an aerobic index and limits.

In some embodiments, the invention provides a method for detecting physiological indices in a user (1), alarming and thereby preventing injuries, characterized by a. providing the user with at least one wearable multiple-sensors IoT device (10) comprising one or more sensors selected from either Group A or [Group A and Group B]; the sensors of Group A are all the three (i)

muscle intensity sensor, (ii) blood pulse sensor, and (iii) skin thermometer; the one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof;

b. by means of a communicator, providing a continuous or a semi- (interval) continuous connection with the multiple-sensors; the communication is provided in direct or mediated protocols and means thereof c. by means of a computer readable database, storing the hereto diagnosed data; and d. by mans of a processor:

i. computing one or more indices from parameters measured by or computed from the sensors;

ii. comparing each of the indices with one or more retrievable limits of the indices, the limits defining at least one allowable range and at least one potentially dangerous range of the index;

iii. if the hereto measured index is within the at least one allowable range, storing the index in the database; and iv. if the hereto measured index is within the at least one potentially dangerous range, both storing the index in the database and alerting the user;

e. by means of one or more alarms, performing the alerting the user; the one or more alarms including light and noise emitters, vibrators or actuators, and any combination thereof; optionally, one or more alarms is configured to alert the user thereby stopping one or many potentially dangerous activities; optionally, additionally or alternatively, one or more alarms is configured to alert user's immediate surroundings, including user's interfaces, user's guides and a combination of the two; optionally, additionally or alternatively, one or more alarms is configured to alert in one or more remote locations, including a remote instructor, ambulance team, physician, friends, family and any combination thereof.

In some embodiments of the method, the blood pulse sensor comprises a PPG.

In some embodiments of the method, the indices and limits are selected from a group consisting of an intensity index and limit, a preparation index and limit, and an aerobic index and limits.

In some embodiments, the invention provides an IoT network for alerting a user of dangerous physiological activity, comprising a. a sensor hive, comprising wearable multi-sensors IoT devices of one or more users, each the multi-sensor IoT device comprising one or more physical sensors, the wearable multi-sensors IoT devices topologically arrangeable in a wirelessly communicatively interconnected tree comprising a slave device and child devices; a processor of the slave device configured to receive live sensor readings from the child devices;

b. a smart device comprising a processor, in communicative connection with the slave device, the smart device processor configured to receive the live sensor data of the wearable multi-sensors IoT devices from the slave device and further configured to manage a power-saving protocol of the slave device and child device in the sensor hive;

c. an algorithm module comprising a processor and a memory comprising live virtual sensors logically integrated with the physical sensors in the multi-sensors IoT devices, each the virtual sensor configured to compute a parameter as a function of readings of one or more of the physical sensors and/or of one or more of other the virtual sensors, the algorithm module in communicative connection with the smart device and with a cloud server, the processor configured to enable the algorithm module to generate warnings as a function of the parameters and past/global data from the cloud server; and further configured to send the warnings to the smart device, the smart device further configured to package the warnings for distribution to the child devices in the sensor hive and send the package to the slave device.

In some embodiments of the network, the algorithm module 115 is further configured to store the live sensor readings in the cloud server 120 for use as future the past/global data.

In some embodiments of the network, the virtual sensors employ a machine algorithm to develop the function for generating the warnings as a function of the past/global.

In some embodiments of the network, the child devices 11W may have up to a maximum number of the child devices (e.g., 8).

In some embodiments of the network, the communicatively interconnected tree employs a protocol selected from a group consisting of Bluetooth, Bluetooth Low Energy, ZigBee, WIFI, 5G, and NFC.

In some embodiments, the network further comprises live panels for displaying current index values from the algorithm module and/or past/global data from the cloud.

In some embodiments of the network, the one or more sensors of a the wearable multiple-sensors IoT device are selected from either Group A or [Group A and Group B]; the sensors of Group A are all the three (i) muscle intensity sensor, (ii) blood pulse sensor, and (iii) skin thermometer; the one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof.

In some embodiments, the invention provides a method for alerting one or more users of dangerous physiological activity, comprising steps of a. providing an IoT network for alerting users of dangerous physiological activity;

b. arranging a sensor hive of one or more wirelessly communicatively interconnected wearable multi-sensors IoT devices into a tree topology of child devices and a slave device;

c. the slave device receiving live sensor readings from physical sensors of the child devices;

d. a smart device receiving the live sensor data of the wearable multi-sensors IoT devices from the slave device;

e. the smart device managing a power-saving protocol of the slave device and child device in the sensor hive;

f. one or more virtual sensors, of an algorithm module, each computing a parameter as a function of readings of one or more of the physical sensors and/or of one or more of other virtual sensors;

g. the algorithm module, in communication with a cloud server, generating warnings as a function of the parameters and past/global data from the cloud server;

h. the algorithm module sending the warnings to the smart device; and i. the smart device packaging the warnings for distribution to child devices in the sensor hive and sending the package to the slave device.

In some embodiments, the method further comprises a step of the algorithm module storing the live sensor readings in the cloud server for use as future past/global data.

In some embodiments, the method further comprises a step of the virtual sensors employing a machine algorithm to develop the function for generating the warnings as a function of the past/global data.

In some embodiments, the method further comprises a step of the child devices having up to a maximum number of child devices (e.g., 8).

In some embodiments, the method further comprises a step of the communicatively interconnected tree employing a protocol selected from a group consisting of Bluetooth, Bluetooth Low Energy, ZigBee, WiFi, 5G, and NFC.

In some embodiments, the method further comprises a step of providing live panels for displaying current index values from the algorithm module and/or past/global data from the cloud.

In some embodiments, the method further comprises a step of selecting one or more the physical sensors of a the wearable multiple-sensors IoT device are selected from either Group A or [Group A and Group B]; the sensors of Group A are all the three (i) muscle intensity sensor, (ii) blood pulse sensor, and (iii) skin thermometer; the one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof.

BRIEF DESCRIPTION OF THE FIGURES

Having thus briefly discussed the invention, a more detailed discussion and description of it follows with reference to the accompanying drawings, which form part of this specification, and of which:

FIG. 4 shows a flow chart of a method for alerting one or more users of dangerous physiological activity, according to some embodiments of the invention.

DETAILED DESCRIPTION OF PREFERRED EMBODIMENTS

In the following description, the same numerical references refer to similar elements. The embodiments, geometrical configurations, materials mentioned and/or dimensions shown in the figures or described in the present description are preferred embodiments only, given for exemplification purposes only.

Figures 1, 2:
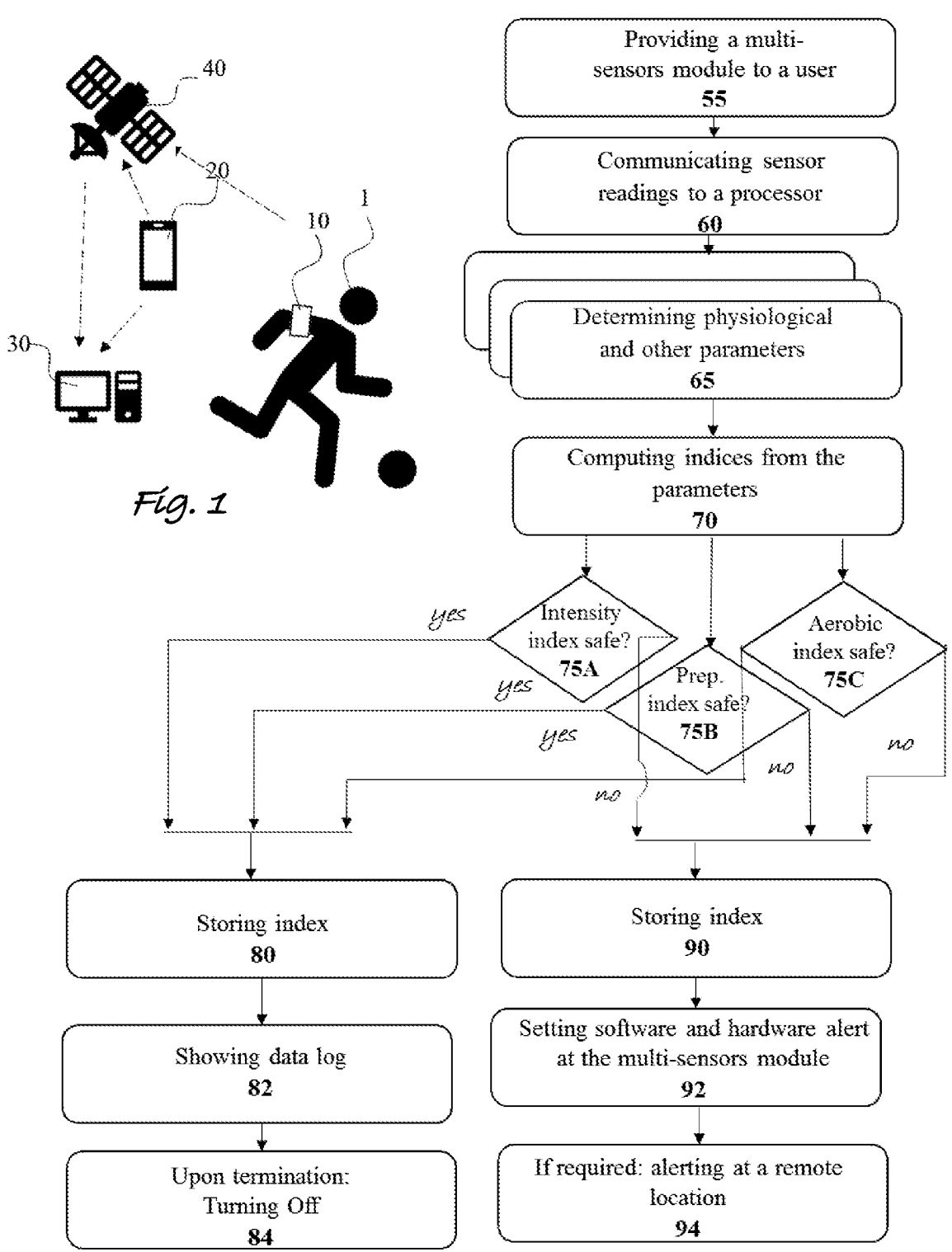
FIG. 1 shows in an out of scale manner one embodiment of the invention, namely a system for synergistically detecting physiological parameters in a user (1), computing indices therefrom, alarming and thereby preventing injuries.
FIG. 2 shows a flow chart of a method for synergistically detecting physiological parameters in a user (1), alarming and thereby preventing injuries according to yet another embodiment of the invention.

Reference is now made to FIG. 1, disclosing in an out of scale manner one embodiment of the invention, namely a system for synergistically detecting physiological parameters in a user (1), computing indices therefrom, alarming and thereby preventing injuries. This system is characterized by a wearable multiple IoT sensors device (10) comprising one or more sensors selected from either Group A and [Group A and Group B]; said sensors of Group A are all the three (i) muscle intensity sensor, (ii) blood pulse sensor, and (iii) skin thermometer. The blood pulse sensor may comprise a photoplethysmogram (PPG), e.g. a blood-content detection PPG, and/or a pulse oximeter. Said one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof.

The system is further characterized by a communicator (20) in a continuous or a semi-(interval) continuous connection with said multiple-sensors (10); said communication is provided in direct (see arrow 10-20) or mediated protocols (arrow 20-30, arrow 20-40) and means thereof.

The system is also characterized by a computer readable database (30) for storing said hereto diagnosed data.

The system still characterized by a processor. The processor is configured for comparing said data obtained from sensors of Group A, and optionally one or more sensors from Group B, with retrievable safe limits defining at least one allowable range and at least one potentially dangerous range of a particular index computed from measurements by the sensors. If said hereto measured index is within said at least one allowable range, storing said index in said database. If said hereto index is within said at least one potentially dangerous range, both storing said index in said database and alerting.

The system is further characterized by one or more alarms, including light and noise emitters, vibrators or actuators, and any combination thereof. Optionally, one or more alarms is configured to alert the user thereby stopping one or many potentially dangerous activities. Still optionally, additionally or alternatively, one or more alarms is configured to alert user's immediate surroundings, including user's interfaces, user's guides and a combination of the two. Also, optionally, additionally or alternatively, one or more alarms is configured to alert in one or more remote locations, including a remote instructor, ambulance team, physician, friends, family and any combination thereof.

Reference is now made to FIG. 2, schematically disclosing a method (50) for synergistically detecting physiological parameters in a user (1), computing indices therefrom, alarming and thereby preventing injuries. This method is characterized by a few steps of operation.

In a first step (55), there is provided the user with at least one set of wearable multiple-sensors IoT device (10) comprising one or more sensors selected from either Group A or [Group A and Group B], Sensors of Group A are all the three (i) muscle intensity sensor, (ii) blood pulse sensor, and (iii) skin thermometer. The blood pulse sensor may comprise a photoplethysmogram (PPG), e.g. a blood-content detection PPG, and/or a pulse oximeter. The one or more sensors of Group B are selected from a group consisting inter alia physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof biological sensors including sweat, secretions, smell test, fluids and gas ($O_2$, $CO_2$, $H_2O$) parameters; and other sensors, including biometric or other identification means, location and time measurements of the user, surroundings and other users and any combination thereof.

Further, and by means of a communicator (20), the for the method further comprises a step (60) of providing a continuous or a semi- (interval) continuous connection with said multiple-sensors (10); said communication is provided in direct (see arrow 10-20) or mediated protocols (arrow 20-30, arrow 20-40) and means thereof.

The method (50) further comprises a step (65) of the remote device (20, 30) determining physiological and other parameters. The parameters may be direct readings from one or more sensors, or computations made therefrom. Step (65) may be alternatively be performed by the device (10), in which case the communicating step (60) entails communicating the parameters.

Further, there is a step (70) of computing indices from the determined parameters.

Then, by mans of a processor, the system is configurable for comparing, for each index, (75A-C) said data obtained from sensors of Group A with a retrievable limit defining at least one allowable range and at least one potentially dangerous range. If said hereto measured index is within said at least one allowable range, storing (80) said index in said database. Optionally, a data log is shown (82). Optionally, to save battery life the device (10) is turned off (84) until a next measurement cycle. If said hereto measured index is within said at least one potentially dangerous range, both storing (90) said index in said database and alerting (92).

By means of one or more alarms, the system is configurable for alarming the user (92) and/or user's adjacent/remote location (94); said one or more alarms including light and noise emitters, vibrators or actuators, and any combination thereof optionally, one or more alarms is configured to alert the user thereby stopping one or many potentially dangerous activities.

Optionally, additionally or alternatively, one or more alarms is configured to alert user's immediate surroundings, including user's interfaces, user's guides and a combination of the two. Still optionally, additionally or alternatively, one or more alarms is configured to alert in one or more remote locations, including a remote instructor, ambulance team, physician, friends, family and any combination thereof.

It is according an embodiment of the invention wherein the processor configured for comparing an index obtained from sensors of Group A, and optionally one or more sensors from Group B, with one or more limits defining at least one allowable range and at least one potentially dangerous range.

In some embodiments, there is an intensity index that indicates the extent to which the user is exerting him-/herself, a preparation index that indicates the extent to which the user prepared for exertion (by warm-up exercises, stretching, etc.) and an aerobic index indicating the degree to which the energy demands of the exertion are met by aerobic metabolism.

In the embodiment described, indices are computed by a product of i parameters measured by or computed from the sensors. In typical embodiments, the number of parameters i is at least 3. However, it is understood that in other embodiments may entail more or fewer parameters and/or one or more different functions, alternatively or in addition.

It is hence in the scope of the invention wherein the limit for Intensity Index, II, is provided herein in a non-limiting manner:

$$II \equiv \prod_{i=1}^{n} pII_i$$

where $pII_i$=is an intensity parameter measured by or computed from the sensors In a non-limiting manner, parameters relevant to intensity index may include one or more of those from EMG, ECG, pulse rate, and strain (measured via blood pressure and/or surface tension).

There is also defined an intensity index limit $L_I$, wherein the following condition is safe:

$$0 \leq II < L_1;$$

and the following condition leads to an alert:

$$L_I \leq II.$$

It is also in the scope of the invention wherein the Preparation Index, PI, is provided herein in a non-limiting manner:

$$PI \equiv \prod_{i=1}^{n} pPI_i$$

where $pPI_i$=is a preparation parameter measured by or computed from the sensors.

In a non-limiting manner, parameters relevant to preparation index may include one or more of those from pulse rate, temperature, $SpO_2$, and blood acidity.

There is also defined a preparation index limit $L_p$, wherein the following condition is safe:

$$PI \geq L_p;$$

and the following condition leads to an alert:

Preparation Index$<L_p$

It is further in the scope of the invention wherein the limit for Aerobic Index, AI, is 360 provided herein in a non-limiting manner:

$$AI \equiv \prod_{i=1}^{n} pAI_i$$

where $pAI_i$=is an aerobic parameter measured by or computed from the sensors.

In a non-limiting manner, parameters relevant to aerobic index may include one or more of those from $SpO_2$, pulse rate, ECG, temperature, and moisture.

There are also defined an aerobic index low limit $L_{A_L}$ and an aerobic index high limit $L_{A_H}$, wherein the following condition is safe:

$$L_{A_L} \leq AI < L_{A_H}$$

and the following condition leads to an alert:

$$AI < L_{A_L} \text{ or } AI \geq L_{A_H}$$

The indices described are above are exemplary only. It is understood that the invention may alternatively, or in addition, compute and alert for one or more other indices related to physical activity.

Figure 3A:
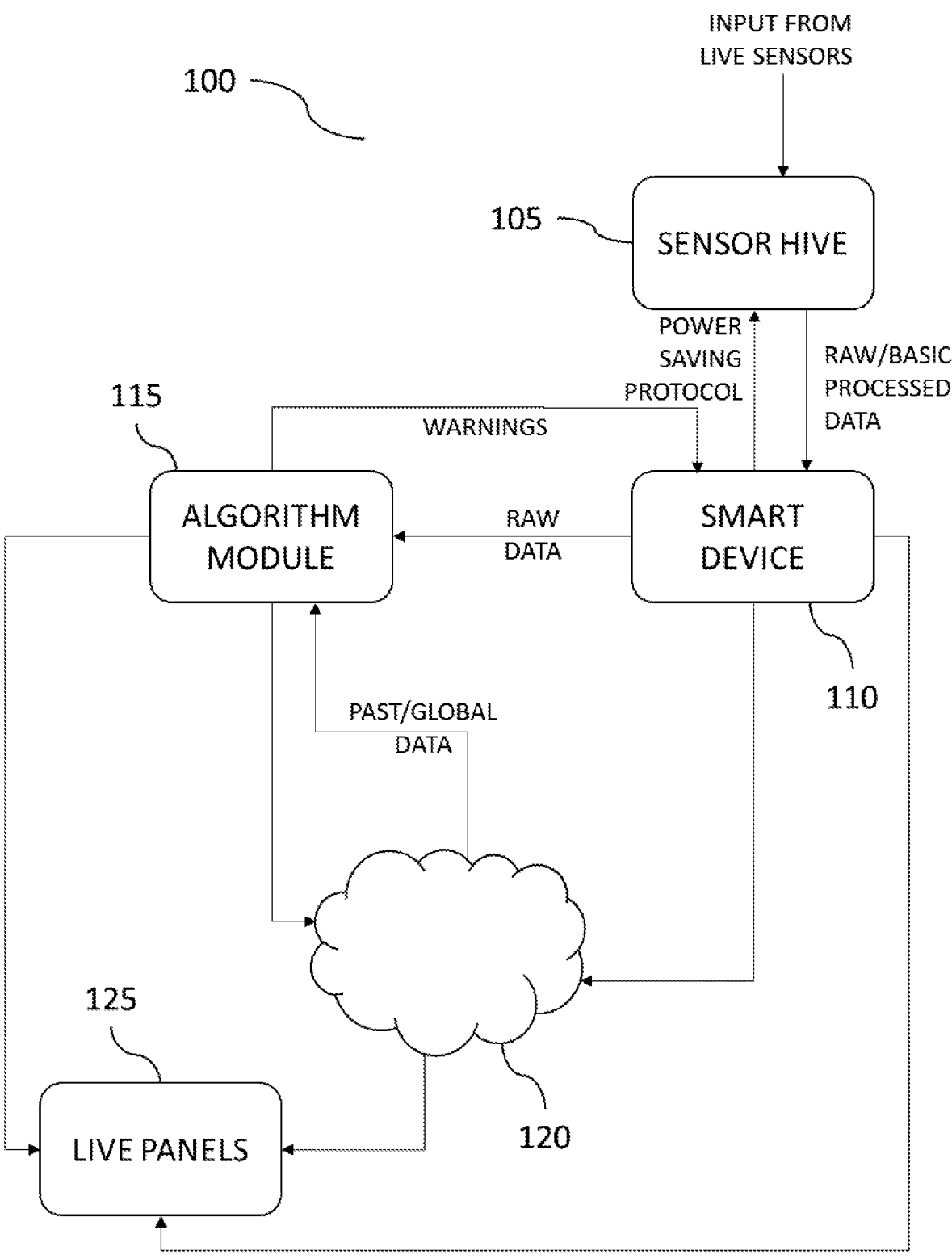
FIG. 3A schematically illustrates a functional block diagram of an IoT network for alerting users of dangerous physiological activity, according to some embodiments of the invention.
Figure 3B:
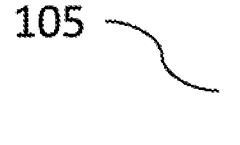
FIG. 3B shows a functional block diagram of a sensor hive of the network.
Figure 3B:
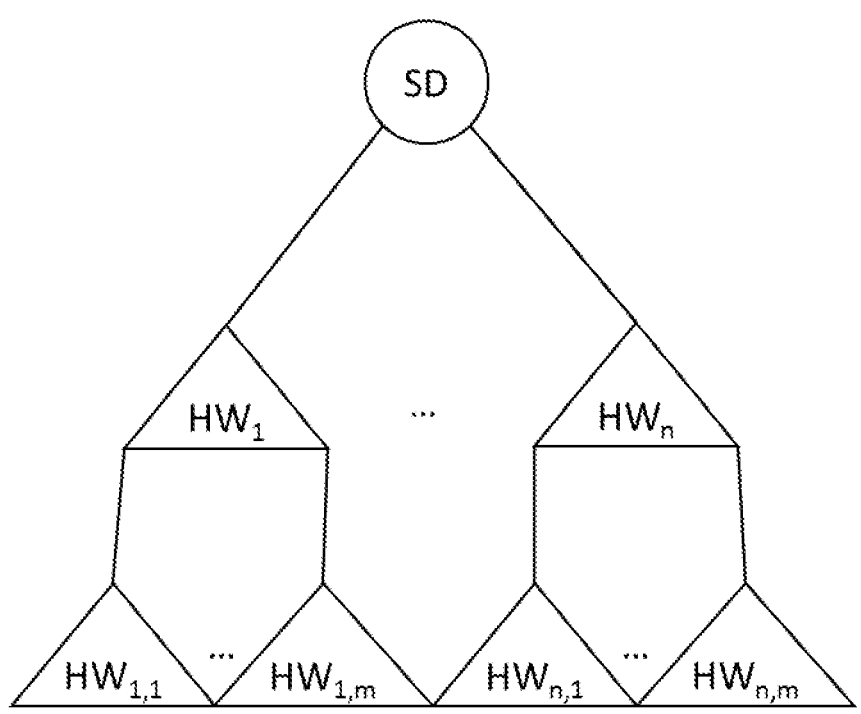

Reference is now made to FIG. 3A, showing a functional block diagram of an IoT network 100 for alerting user of dangerous physiological activity, and FIG. 3B, showing a functional block diagram of a sensor hive 105 of the network 100.

The sensor hive 105 comprises wearable multi-sensors IoT devices of one or more users. The multi-sensors IoT devices may be equivalent or similar to the ones described above. Each multi-sensor IoT device comprises one or more sensors. The wearable multi-sensors IoT devices are wirelessly communicatively interconnected and arrange themselves topologically into a tree comprising a slave device SD and child devices HW. The slave device SD receives live sensor readings from the sensors of the child devices HW.

The wireless interconnection may be of any suitable protocol, including (but not exclusively) Bluetooth, Bluetooth Low Energy, ZigBee, WiFi, 5G and/or NFC. The number of child devices HW of the slave device SD may be limited to some number n. The maximum number of child devices HW of other child devices HW may be limited to some number m; in some present implementations, the limit m is eight. Typically, the limit n is greater than the limit m. While the sensor hive 105 of FIG. 3B shows two tree-layers of child devices HW, it is understood that in some other embodiments of the sensor hive 105 the number of tree-layers of child device 105 may be greater than two.

The IoT network 100 further comprises a smart device 110, with a processor, in communicative connection with the slave device SD. The smart device 110 receives the live sensor data of the wearable multi-sensors IoT devices from the slave device SD. Optionally, the smart device 110 manages a power-saving protocol of the sensor hive 105.

Figure 3C:
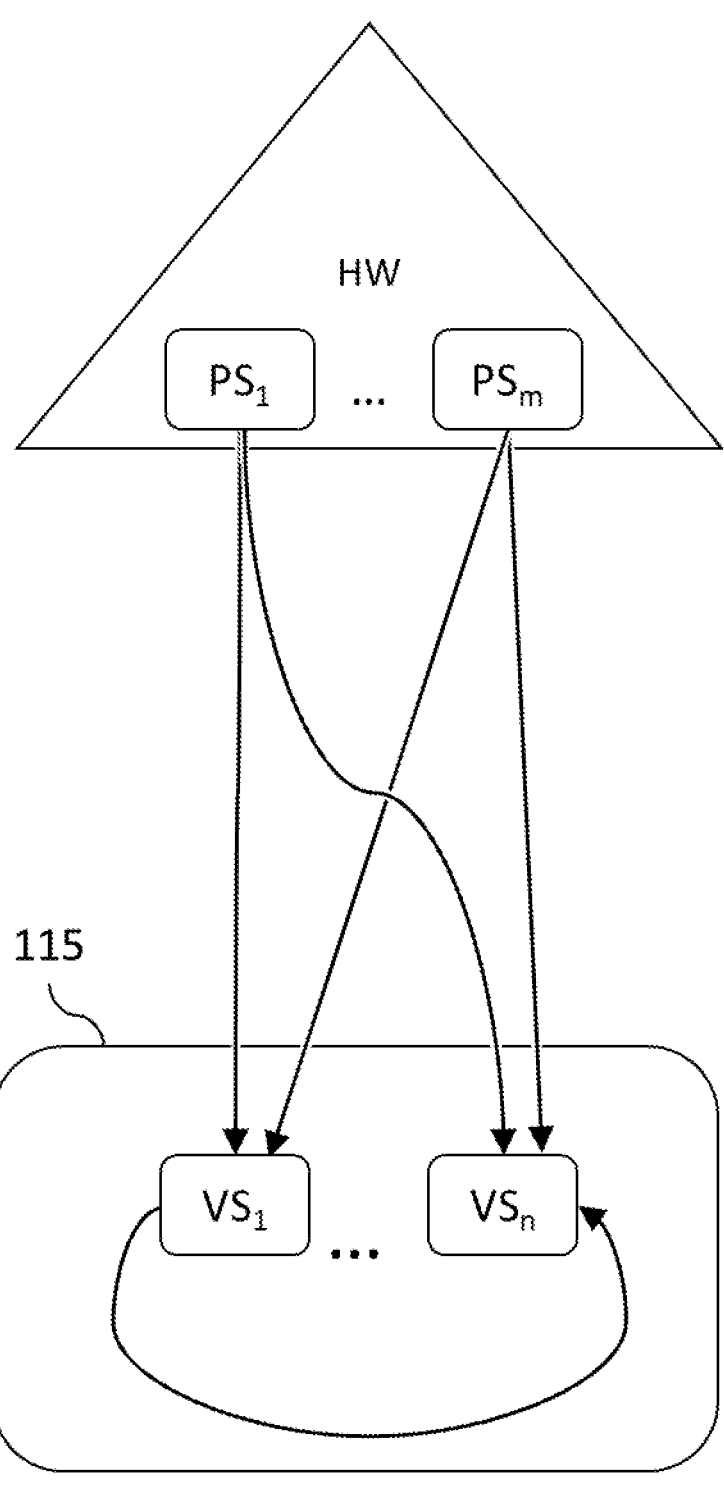
FIG. 3C shows the inter-relationship between physical sensors in multi-sensors IoT devices in and virtual sensors in the algorithm module of the network.

The IoT network 100 further comprises an algorithm module 115, with a processor and memory containing live virtual sensors that are logically integrated with physical sensors in the multi-sensors IoT devices. FIG. 3C shows the inter-relationship between physical sensors PS in the multi-sensors IoT devices HW and virtual sensors VS in the algorithm module 115. Each virtual sensor processes outputs of one or more physical sensors PS and/or one or more other virtual sensor VS. Each virtual sensor VS comprises a memory storing instructions of an algorithm to generate a parameter from the outputs of the relevant physical sensors PS and/or other virtual sensors VS. The algorithm module 115 computes indices from the parameters—as further described herein—generated by the virtual sensors VS. It is noted that a parameter may also be the output of a physical sensor PS.

The algorithm module 115 further computes warnings to a user, the warnings generated as a function of the live sensor readings of the user's multi-sensors IoT device and past/global data (e.g., past sensor data and the retrievable limits) from the cloud server 120. The algorithm module 115 sends the warnings to the smart device 110. The smart device 110 in turn packages the warnings for distribution to the child devices in the sensor hive 105 and sends the package to the slave device SD. Each child device 11W opens its own warning(s) and alerts its user accordingly and passes the remaining warnings of the package to its own child devices 11W. The process cascades through the sensor hive 105 until a leaf of the tree is reached.

In FIG. 3B, there are two layers of children devices. There may be limits to the number of devices at each layer. For example, the first layer is limited to n devices and the second layer is limited to m devices, as shown. Typically, m is limited to a smaller number (e.g. 8) than n, which can be a much higher number. While In some embodiments, the algorithm module 115 stores readings of the live physical sensor PS and/or live virtual sensors VS to the cloud server 120. The virtual sensors may employ a machine algorithm to develop or refine the function parameters P, used to calculate the indices, and the limits L, as further described herein, for generating the warnings.

In some embodiments, the network 100 further comprises live panels 125, displaying current index values from the algorithm module 115 and/or past/global data from the cloud 120. The live panels 125 may be incorporated in smart device 110 and/or in another smart device or computing device. Live panels 125 enable convenient live viewing by interested parties—such as coaches and trainers—of athletes' exertion.

Reference is now made to FIG. 4, showing a method for alerting one or more users of dangerous physiological activity. The method 200 comprises steps of a. providing an IoT network for alerting users of dangerous physiological activity 205;

b. arranging a sensor hive of one or more wirelessly communicatively interconnected wearable multi-sensors IoT devices into a tree topology of child devices and a slave device 210;

c. the slave device receiving live sensor readings from physical sensors of the child devices 215;

d. a smart device receiving the live sensor data of the wearable multi-sensors IoT devices from the slave device 220;

e. the smart device managing a power-saving protocol of the slave device and child device in the sensor hive 225;

f. one or more virtual sensors, of an algorithm module, each computing a parameter as a function of readings of one or more of the physical sensors and/or of one or more of other virtual sensors 230;

g. the algorithm module, in communication with a cloud server, generating warnings as a function of the parameters and past/global data from the cloud server 235;

h. the algorithm module sending the warnings to the smart device 240; and i. the smart device packaging the warnings for distribution to the child devices in the sensor hive and sending the package to the slave device 245.

As used in the specification and the appended claims, the singular forms "a," "an" and "the" include their plural referents unless the context clearly dictates otherwise. The terms "comprising" or "containing" or "consisting" or "including" are understood to mean that at 430 least the named sensors, limits, method steps, etc., is present in the composition or article or method, but does not exclude the presence of other sensors, PCBs, limits, method steps, etc., even if the other such other sensors, limits, method steps have the same function as what is named, unless expressly excluded in the claims.

It is also understood that the mention of one or more method steps does not preclude 435 the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

The invention claimed is:

1. A system for detecting physiological indices in a user (1), alarming and thereby preventing injuries, characterized by:

a. a wearable multiple-sensors IoT device (10) comprising one or more sensors selected from either Group A or Group B; said sensors of Group A are all the three (i) muscle intensity sensor, (ii) blood pulse sensor, and (iii) skin thermometer, said sensors deployed directly on muscles and tissues relevant to a specific sport or exercise based on a predetermined biomechanical mapping; said one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas (O2, CO2, H2O) parameters; and other sensors, including biometric or other identification means, location and time measurements of the user, surroundings and other users and any combination thereof;

b. a communicator (20) in a continuous or a semi-(interval) continuous connection with said multiple-sensors (10); said communication is provided in direct (10-20) or mediated protocols (20-30, 20-40) and means thereof;

c. a computer readable database (30) for storing said hereto diagnosed data; and d. a processor configured for:

i. computing one or more mathematically defined, quantitative, multi-factorial predictive indices from parameters measured by or computed from said sensors, wherein said indices are indicative of a risk of sport injury and are derived from the combined analysis of muscle intensity, blood pulse, and skin temperature data, and wherein said indices are specifically tailored to the context of sports and physical activity;

ii. comparing each of said indices with one or more predefined and retrievable limits of said index, said limits defining at least one allowable range and at least one potentially dangerous range of said index, wherein said limits are dynamically updated using machine learning based on user-specific, sport-specific, and historical data;

iii. if said hereto measured index is within said at least one allowable range, storing said index in said database; and iv. if said hereto measured index is within said at least one potentially dangerous range, both storing said index in said database and alerting the user to enable avoidance of future sport injuries before actual damage occurs; and e. one or more alarms for said alerting of the user, including light and noise emitters, vibrators or actuators, and any combination thereof, said alarms configured to provide immediate, multi-channel alerts and to stop or modify potentially dangerous activities in real time; optionally, one or more alarms is configured to alert the user thereby stopping one or many potentially dangerous activities; optionally, additionally or alternatively, one or more alarms is configured to alert user's immediate surroundings, including user's interfaces, user's guides and a combination of the two; optionally, additionally or alternatively, one or more alarms is configured to alert in one or more remote locations, including a remote instructor, ambulance team, physician, friends, family and any combination thereof.

2. The system of claim 1, wherein said blood pulse sensor comprises a PPG, a pulse oximeter, or any combination thereof, wherein said PPG or pulse oximeter is specifically configured to contribute to the multi-factorial predictive indices for sport injury risk in combination with muscle intensity and skin temperature data, and wherein the system processes data from said sensors at ultra-high sampling rates (tens to thousands of samples per second) for sub-second, multi-dimensional assessment.

3. The system of claim 1, wherein said indices and limits are selected from a group consisting of an intensity index and limit, a preparation index and limit, and an aerobic index and limits, each mathematically defined and computed from multiple, high-frequency sensor signals, and wherein said indices are specifically configured to predict and prevent sport-related musculoskeletal injuries based on the physiological state of the user during physical activity.

4. A method for detecting physiological indices in a user (1), alarming and thereby preventing injuries, characterized by:

a. providing said user with at least one wearable multiple-sensors IoT device (10) comprising one or more sensors selected from either Group A or Group B; said sensors of Group A are all the three (i) muscle intensity sensor, (ii) blood pulse sensor, and (iii) skin thermometer, said sensors deployed directly on muscles and tissues relevant to a specific sport or exercise based on a predetermined biomechanical mapping; said one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof;

b. by means of a communicator (20), providing a continuous or a semi-(interval) continuous connection with said multiple-sensors (10); said communication is provided in direct (10-20) or mediated protocols (20-30, 20-40) and means thereof;

c. by means of a computer readable database (30), storing said hereto diagnosed data; and d. by means of a processor:
   i. computing one or more mathematically defined, quantitative, multi-factorial predictive indices from parameters measured by or computed from said sensors, wherein said indices are indicative of a risk of sport injury and are derived from the combined analysis of muscle intensity, blood pulse, and skin temperature data, and wherein said indices are specifically tailored to the context of sports and physical activity;
   ii. comparing each of said indices with one or more predefined and retrievable limits of said indices, said limits defining at least one allowable range and at least one potentially dangerous range of said index, wherein said limits are dynamically updated using machine learning based on user-specific, sport-specific, and historical data;
   iii. if the hereto measured index is within said at least one allowable range, storing said index in said database; and
   iv. if the hereto measured index is within said at least one potentially dangerous range, both storing said index in said database and alerting the user to enable avoidance of future sport injuries before actual damage occurs;

e. by means of one or more alarms, performing said alerting the user, said alarms configured to provide immediate, multi-channel alerts and to stop or modify potentially dangerous activities in real time; said one or more alarms including light and noise emitters, vibrators or actuators, and any combination thereof; optionally, one or more alarms is configured to alert the user thereby stopping one or many potentially dangerous activities; optionally, additionally or alternatively, one or more alarms is configured to alert user's immediate surroundings, including user's interfaces, user's guides and a combination of the two; optionally, additionally or alternatively, one or more alarms is configured to alert in one or more remote locations, including a remote instructor, ambulance team, physician, friends, family and any combination thereof.

5. The method of claim 4, wherein said blood pulse sensor comprises a PPG, a pulse oximeter, or any combination thereof, wherein said PPG or pulse oximeter is specifically configured to contribute to the multi-factorial predictive indices for sport injury risk in combination with muscle intensity and skin temperature data, and wherein the system processes data from said sensors at ultra-high sampling rates (tens to thousands of samples per second) for sub-second, multi-dimensional assessment.

6. The method of claim 4, wherein said indices and limits are selected from a group consisting of an intensity index and limit, a preparation index and limit, and an aerobic index and limits, each mathematically defined and computed from multiple, high-frequency sensor signals, and wherein said indices are specifically configured to predict and prevent sport-related musculoskeletal injuries based on the physiological state of the user during physical activity.

7. An IoT network 100 for alerting users of dangerous physiological activity, comprising:
   a. a sensor hive 105, comprising wearable multi-sensors IoT devices of one or more users, each said multi-sensor IoT device comprising one or more physical sensors PS, said wearable multi-sensors IoT devices topologically arrangeable in a wirelessly communicatively interconnected tree comprising a slave device SD and child devices HW; a processor of said slave device SD configured to receive live sensor readings from said child devices HW;
   b. a smart device 110 comprising a processor, in communicative connection with said slave device SD, said smart device processor configured to receive said live sensor data of the wearable multi-sensors IoT devices from said slave device SD and further configured to manage a power-saving protocol of said slave device SD and child device HW in said sensor hive 105;
   c. an algorithm module 115 comprising a processor and a memory comprising live virtual sensors logically integrated with said physical sensors PS in said multi-sensors IoT devices, each said virtual sensor VS configured to compute a parameter as a function of readings of one or more of said physical sensors PS and/or of one or more of other said virtual sensors VS, said algorithm module 115 in communicative connection with said smart device 110 and with a cloud server 120, said processor configured to enable said algorithm module 115 to generate predictive warnings of impending sport injuries based on the combined analysis of muscle intensity, blood pulse, and skin temperature data, and wherein said warnings are derived from mathematically defined, quantitative indices specifically tailored to the context of sports and physical activity as a function of said parameters and past/global data from said cloud server 120; and further configured to send said warnings to said smart device, said smart device further configured to package said warnings for distribution to said child devices in said sensor hive 105 and send said package to said slave device SD.

8. The network of claim 7, wherein said algorithm module 115 is further configured to store said live sensor readings in said cloud server 120 for use as future said past/global data, and wherein said cloud server and associated analytics modules enable automatic data backup, sharing with professional staff (such as coaches and physiotherapists), and historical analysis for ongoing improvement of training and injury prevention recommendations.

9. The network of claim 7, wherein the virtual sensors employ a machine algorithm to develop said function for generating said predictive warnings of impending sport injuries based on the combined analysis of muscle intensity, blood pulse, and skin temperature data, and wherein said machine learning is leveraged for optimizing training regimens and injury prevention strategies as a function of said past/global data.

10. The network of claim 7, wherein said child devices HW may have up to a maximum number of child devices (e.g., 8), and wherein the IoT network supports a sensor hive topology for centralized management of alerts and energy efficiency in team or group sports scenarios.

11. The network of claim 7, wherein said communicatively interconnected tree employs a protocol selected from a group consisting of Bluetooth, Bluetooth Low Energy, BLE (Bluetooth Low Energy) Mesh, ZigBee, WiFi, 5G, and NFC.

12. The network of claim 7, further comprising live panels for displaying current index values from the algorithm module and/or past/global data from the cloud 120, wherein said index values are indicative of sport injury risk and are derived from mathematically defined, quantitative indices specifically tailored to the context of sports and physical activity.

13. The network of claim 7, wherein said one or more sensors of a said wearable multiple-sensors IoT device are selected from either Group A or Group B; said sensors of Group A are all the three (i) muscle intensity sensor, (ii) blood pulse sensor, and (iii) skin thermometer, said sensors deployed directly on muscles and tissues relevant to a specific sport or exercise based on a predetermined biomechanical mapping; said one or more sensors of Group B are selected from physiological sensors, including blood parameters other than heart pulse rate, blood oxidation, blood flow rate, blood flow parameters, acoustics and doppler thereof, blood composition, impedance, AKG, EEG, PPG, ECG, electrical-wave measurements, and any combination thereof; physical sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas (O2, CO2, H2O) parameters; and other sensors, including biometric or other identification means, location and time measurements of the user, surroundings and other users and any combination thereof.

14. A method 200 for alerting one or more users of dangerous physiological activity, comprising steps of:
a. providing an IoT network 100 for alerting users of dangerous physiological activity, comprising:
i. a sensor hive 105, comprising wearable multi-sensors IoT devices of one or more users, each said multi-sensor IoT device comprising one or more physical sensors PS, said wearable multi-sensors IoT devices topologically arrangeable in a wirelessly communicatively interconnected tree comprising a slave device SD and child devices HW; a processor of said slave device SD configured to receive live sensor readings from said child devices HW;
ii. a smart device 110 comprising a processor, in communicative connection with said slave device SD, said smart device processor configured to receive said live sensor data of said wearable multi-sensors IoT devices from said slave device SD and further configured to manage a power-saving protocol of said slave device SD and child device HW in said sensor hive 105;

iii. an algorithm module 115 comprising a processor and a memory comprising live virtual sensors logically integrated with said physical sensors PS in said multi-sensors IoT devices, each said virtual sensor VS configured to compute a parameter as a function of readings of one or more of said physical sensors PS and/or of one or more of other said virtual sensors VS, said algorithm module 115 in communicative connection with said smart device 110 and with a cloud server 120, said processor configured to enable said algorithm module 115 to generate predictive warnings of impending sport injuries based on the combined analysis of muscle intensity, blood pulse, and skin temperature data, and wherein said warnings are derived from mathematically defined, quantitative indices specifically tailored to the context of sports and physical activity as a function of said parameters and past/global data from said cloud server 120; and further configured to send said warnings to said smart device, said smart device further configured to package said warnings for distribution to said child devices in said sensor hive 105 and send said package to said slave device SD;
b. arranging a sensor hive of one or more wirelessly communicatively interconnected wearable multi-sensors IoT devices into a tree topology of child devices and a slave device 210;
c. the slave device receiving live sensor readings from physical sensors of the child devices 215;
d. a smart device receiving the live sensor data of said wearable multi-sensors IoT devices from said slave device 220;
e. the smart device managing a power-saving protocol of said slave device and child device in said sensor hive 225;
f. one or more virtual sensors, of an algorithm module, each computing a parameter as a function of readings of one or more of said physical sensors and/or of one or more of other said virtual sensors 230;
g. the algorithm module, in communication with a cloud server, generating predictive warnings of impending sport injuries based on the combined analysis of muscle intensity, blood pulse, and skin temperature data, and wherein said warnings are derived from mathematically defined, quantitative indices specifically tailored to the context of sports and physical activity as a function of said parameters and past/global data from the cloud server 235;
h. the algorithm module sending the warnings to the smart device 240; and
i. the smart device packaging the warnings for distribution to said child devices in said sensor hive and sending the package to said slave device 245.

15. The method of claim 14, further comprising a step of said algorithm module storing said live sensor readings in said cloud server for use as future said past/global data, and wherein said cloud server and associated analytics modules enable automatic data backup, sharing with professional staff (such as coaches and physiotherapists), and historical analysis for ongoing improvement of training and injury prevention recommendations.

16. The method of claim 14, further comprising a step of the virtual sensors employing a machine algorithm to develop said function for generating said predictive warnings of impending sport injuries based on the combined analysis of muscle intensity, blood pulse, and skin temperature data, and wherein said machine learning is leveraged for optimizing training regimens and injury prevention strategies as a function of said past/global data.

17. The method of claim 14, further comprising a step of said child devices having up to a maximum number of child devices (e.g., 8), and wherein the IoT network supports a sensor hive topology for centralized management of alerts and energy efficiency in team or group sports scenarios.

18. The method of claim 14, further comprising a step of said communicatively interconnected tree employing a protocol selected from a group consisting of Bluetooth, Bluetooth Low Energy, BLE (Bluetooth Low Energy) Mesh, ZigBee, WiFi, 5G, and NFC.

19. The method of claim 14, further comprising a step of providing live panels for displaying current index values from the algorithm module and/or past/global data from the cloud, wherein said index values are indicative of sport injury risk and are derived from mathematically defined, quantitative indices specifically tailored to the context of sports and physical activity.

20. The method of claim 14, further comprising a step of selecting one or more said physical sensors of a said wearable multiple-sensors IoT device are selected from either Group A or Group B; said sensors of Group A are all the three (i) muscle intensity sensor, (ii) blood pulse sensor, and (iii) skin thermometer, said sensors deployed directly on muscles and tissues relevant to a specific sport or exercise based on a predetermined biomechanical mapping; said one or more sensors of Group B are selected from physiological sensors, including user location, user movement at any 2D plane or 3D orientation, acceleration, time, ambient temperature, ambient humidity, and wind conditions, a sensor's or body's organ movement and profile thereof; biological sensors including sweat, secretions, smell test, fluids and gas ($O_2$, $CO_2$, $H_2O$) parameters; and other sensors, including biometric or other identification means, location and time measurements of the user, surroundings and other users and any combination thereof.

\* \* \* \* \*